United States Patent [19]

Wilson

[11] 4,271,406
[45] Jun. 2, 1981

[54] BED WETTING TATTLER

[76] Inventor: Reginald D. Wilson, 2601 Roslyn Ave., Baltimore, Md. 21216

[21] Appl. No.: 62,489

[22] Filed: Jul. 31, 1979

[51] Int. Cl.³ .............................................. G08B 21/00
[52] U.S. Cl. .................................. 340/604; 128/138 A
[58] Field of Search ...................... 340/604, 603, 620; 200/61.05, 61.04; 128/138 A, 138 R

[56] References Cited

U.S. PATENT DOCUMENTS

| | | | |
|---|---|---|---|
| 2,726,294 | 12/1955 | Kroening et al. | 340/604 |
| 2,907,841 | 10/1959 | Campbell | 200/61.05 |
| 3,037,165 | 5/1962 | Kerr | 340/620 |
| 3,245,068 | 4/1966 | Wegryn et al. | 340/604 |
| 3,441,019 | 4/1969 | Snyder | 340/604 |
| 3,778,570 | 12/1973 | Shuman | 200/61.05 |
| 3,810,140 | 5/1974 | Finley | 340/604 |
| 4,069,817 | 1/1978 | Fenole et al. | 340/604 |
| 4,106,001 | 8/1978 | Mahoney | 340/604 |
| 4,163,449 | 8/1979 | Regal | 340/604 |

FOREIGN PATENT DOCUMENTS 222939 7/1959 Australia ................................ 340/604

Primary Examiner—Gerald L. Brigance
Attorney, Agent, or Firm—D. Paul Weaver

[57] ABSTRACT

A system for providing an alarm in the event of a bed wetting occurrence is presented which includes a pair of electrodes fabricated from permanent magnets which are positioned adjacent to each other and held apart by a thin spacer. A self-latching relay is responsive to the completion of an electrical circuit between the electrodes which during the normal application of the invention is caused by an electrolyte such as urine. The self-latching relay interrupts current flow to the magnetic electrodes and activates a nurses call system through the use of pulsating signals.

11 Claims, 4 Drawing Figures

BED WETTING TATTLER

THE INVENTION

This invention relates to a means to provide an alarm to signify a bed wetting occurrence.

BACKGROUND OF THE INVENTION

Modern technology has produced a wide variety of electronic devices for alerting nurses to various difficulties encountered by patients. Among those devices are means responsive to bed wetting occurrences.

For instance, Wegryen in U.S. Pat. No. 3,245,068 discloses the concept of utilizing a paper sheet having a printed circuit thereon which can be placed beneath a patients body and connected to a suitable alarm means. When an electrolyte saturates the paper on which the circuit is printed, the alarm is activated.

Macias in U.S. Pat. No. 3,864,676 is exemplary of prior art systems which use an elongated sensor that is attached to the clothing of a patient and cause completion of an electarical circuit in the presence of an electrolyte.

The Seiger patent, U.S. Pat. No. 2,127,538 is exemplary of the prior art systems where a pad is provided with a plurality of electrical contacts and adapted to be placed under a patient. The electrical contacts are bridged by the presence of an electrolyte and cause the activation of alarm. Devices such as the Seiger device are fabricated so that they can be removed for cleaning.

All of the preceeding bed wetting alarms are limited to their use and application by their physical structure and require an excessive amount of fabrication detail which causes their cost to be high and their reliability low.

OBJECTIVES OF THE INVENTION

In view of the obvious limitations of the various bed wetting alarms of the prior art systems and the complexities and expense involved in their manufacture, it is a primary objective of the present invention to provide a bed wetting alarm which may be readily adapted to a large variety of environments while incorporating design concepts that render it inexpensive to manufacture.

A further objective of the present invention is to provide a moisture sensing means comprising a pair of electrodes constructed of a magnetic material wherein at least one electrode is a permanent magnet generating a magnetic field having sufficient strength to hold the two electrodes in close approximation.

A still further objective of the present invention is to provide a moisture sensing alarm which includes a self-holding relay that will provide a signal to an existing alarm system and disconnect electrical current flow to the sensing electrodes when the system is energized.

It is a further objective of the present invention to provide a moisture sensing alarm which may be fastened to bed clothing or a user's clothing by positioning a magnetic electrode on either side of the cloth material of which the bed clothing or user's clothing is fabricated.

The foregoing and other objectives of the invention will become apparent in light of the drawings, specification and claims contained herein.

SUMMARY OF THE INVENTION

Presented hereby is a moisture sensing alarm comprised of a pair of electrodes fabricated from a magnetic material wherein at least one electrode is a permanent magnet generating a field sufficiently strong to hold the two electrodes together with a spacing element therebetween. When the electrical gap between the electrodes is bridged by an electrolyte, an electrical circuit is completed to energize a self-holding relay which, in turn activates an alarm which may be a means which pulses an existing alarm system.

When activated, the self-holding relay of the present invention removes the source of current to the moisture sensing electrodes but maintains energizing current flow through its coil until reset.

DESCRIPTION OF THE INVENTION

Figure 1:
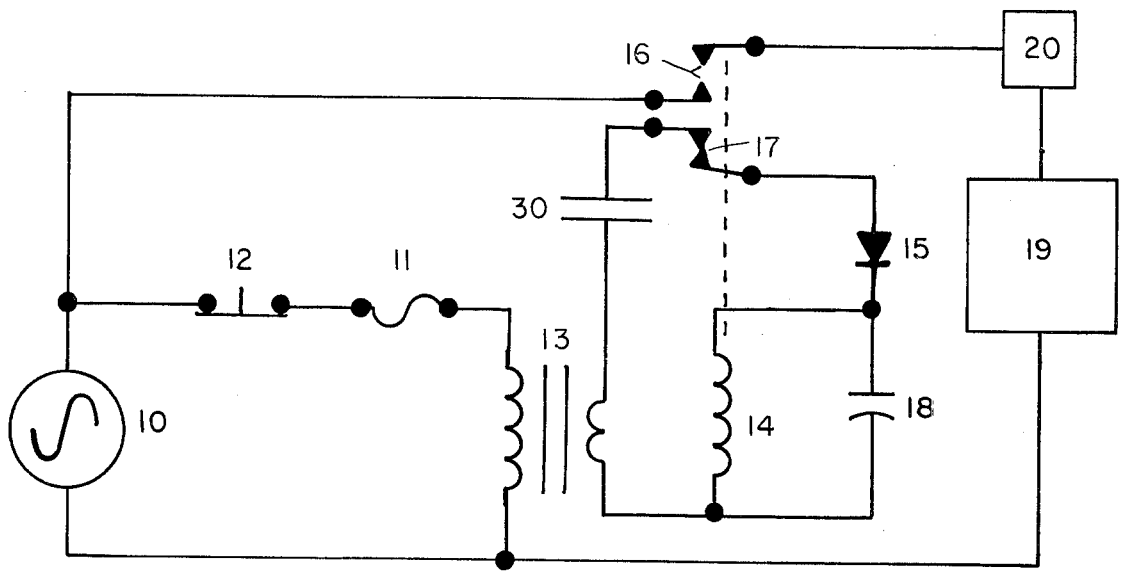
FIG. 1 is a schematic diagram representing the electrical circuit of the present invention.

FIG. 1 illustrates the schematic of a typical installation of the bed wetting tattler. In a preferred embodiment, alternating current is applied from any convenient source 10 but it should be understood that if desired, DC components may be utilized in the circuitry and the system powered by any convenient DC source.

In the preferred embodiment of FIG. 1, standard AC current from source 10 is coupled through a control switch 12 and safety fuse 11 to step down transformer 13. Step down transformer 13 provides a low voltage, low current source for relay 14 which includes normally opened contact pair 16 and normally closed contact pair 17.

Relay contact pair 17 may be low current contact points because current flow through the system is limited by fuse 11 which is calculated to prevent current flow through the system from exceeding a value which would cause discomfort or electrical shock to a person coming in contact with sensor electrodes 30.

Contact set 16 is not protected by fuse 11 and must be capable of carrying the current which is required by alarm means 19 and timer 20.

Switch 12 is a standard commercially available switch having a spring loaded, normally closed position and an activating mechanism whereby an operator may momentarily press the switch to a first, spring loaded detent position whereby the circuit is interrupted and the alarm system reset and upon release of the switch activating lever, the switch will return to the normally closed position. If the operator prefers, the switch activating lever may be pressed through the first detent to an off position which will disable the system until it is returned to the spring biased mode.

The low current, low voltage from the secondary of transformer 13 is applied through the moisture sensing electrodes 30 to the normally closed relay contacts 17. If an electrolyte is present between the electrodes, current will flow therebetween, through contacts 17 and the coil of relay 14, causing the coil to energize and open normally closed contacts 17. When normally closed contacts 17 open, current flow to electrodes 30 and coil 14 is interrupted. Relay 14 will be deenergized by contacts 17 opening but the relay is a mechanically latching relay such as an AMF Potter & Brunfield R10 series and when tripped by being energized, it will remain in the tripped position until manually reset.

With relay 14 tripped, normally open switch contacts 16 are closed and current is provided to an alarm means 19 via timer means 20. Timer means 20 may be a thermally activated blinker system such as is normally incorporated in commercially available light flashers or it may be an electronic timer adapted to produce a continual series of pulses. The pulsed current from timer 20 activates alarm means 19 in a pulsating fashion to attract the attention of a person who is suppose to be monitoring the alarm system.

In a preferred embodiment, alarm means 19 is the normally installed nurse calling light in a hospital or nursing home installation and timer 20 activates the specific light related to the bed associated with the electrode pair 30 in a flashing fashion to provide an indication to the nurse that the light is illuminated as a function of the bed wetting tattler as opposed to the illumination of the light created by the patients call switch. If desired, audio alarm means may also be incorporated in alarm means 19.

Figure 2:
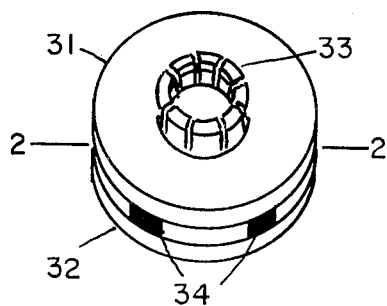
FIG. 2 is a top view of the magnetic electrode assembly.
Figure 3:
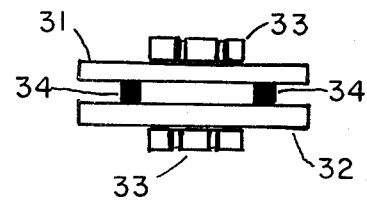
FIG. 3 is a sectional view of the magnetic electrode assembly of FIG. 2 taken along lines 2—2.
Figure 4:
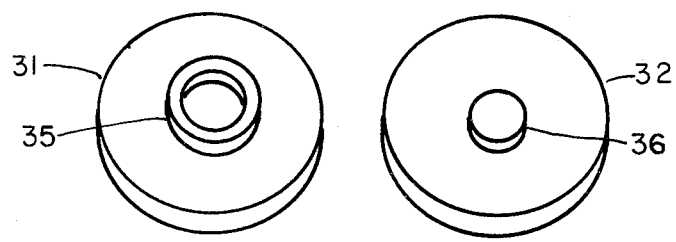
FIG. 4 illustrates the contact sides of an alternate embodiment of the electrodes of the present invention.

The electrode pair 30 of FIG. 1 is comprised of a pair of electrodes 31 and 32 of FIGS. 2, 3 and 4 which may be of any convenient shape. The electrodes have approximately equal surface area and are fabricated from a magnetic material. At lease one of the electrodes is a permanent magnet and in a preferred embodiment both electrodes are permanent magnets. Each electrode includes a snap fastener 33 by which an insulated conductor may be mechanically and electrically connected to the electrode. In a preferred embodiment, a standard 9 volt transistor radio battery snap fastener is secured to the magnetic disc forming an electrode.

A null spacer approximately three-thousandth of an inch thick is positioned on each electrode off center and on the side opposite the electrical connector. This spacer, 34, may best be seen in FIG. 3 which is a cutaway view of the electrode assembly. Note that the spacer on each of the facing electrodes hold the contact faces of electrodes 31 and 32 parallel to each other and provide space therebetween wherein in electrolyte may flow to complete an electrical circuit. Spacers 34 are fabricated from any known insulating material.

In a preferred embodiment, electrodes 31 and 32 are fabricated identical to each other to simplify the manufacturing and supply process and include off-center spacers which permit any two electrodes to be assembled as illustrated in FIG. 3 with the magnetic forces exerted by the material from which the electrodes are fabricated functioning as the means to hold the two electrodes together.

Alternate embodiments of the invention may be utilized wherein electrical connection is made by a variety of mechanical and electrical connection means and only one of the electrodes need be a permanent magnet.

A further alternate embodiment of the present invention is considered wherein spacers 34 of FIG. 3 are comprised of the bed clothing or clothing of the user. In this embodiment, the electrodes are merely placed on opposite sides of a piece of cloth and the magnetic attraction between the electrodes securely holds them in place with the cloth forming spacers 34. In the event the cloth becomes saturated with an electrolyte, an electrical path is completed between the electrodes and the alarm is activated as previously described with respect to the schematic of FIG. 1. This mode of operation may also be employed if spacers 34 are insulator means actucally secured to electrodes 31 and/or 32. If this is the case, the spacers function to interlock the two electrodes and prevent their being forced apart by a sliding action of the user over an electrode face.

FIG. 4 is an alternate embodiment wherein electrodes 30 and 31 are provided with interlocking insulative spacers. In this embodiment, electrode 31 is provided with a ring shaped insulator 35 which is centrally located on the contact surface of the electrode and electrode 32 is provided with a centrally located insulator 36 dimensioned to fit within the ring of insulator 35 so that when the two electrodes are positioned adjacent to each other the insulators form an interlocking spacer which will prevent lateral forces from separating the electrodes. Note that the outer dimension of ring insulator 35 is sufficiently smaller than the dimension of electrodes 31 and 32 so that sufficient contact surfaces are exposed whereby a circuit may be completed by an electrolyte.

While preferred embodiments of this invention have been illustrated and described, variations and modifications may be apparent to those skilled in the art. Therefore, I do not wish to be limited thereto and ask that the scope and breadth of this invention be determined from the claims which follow rather than the above description.

What I claim is:

1. A moisture sensing apparatus, comprising:
   a latching relay including a coil, a set of normally open electrical contacts, and a set of normally closed electrical contacts;
   a source of electrical current;
   a first electrode electrically connected to said source of electrical current;
   a second electrode electrically connected to said relay coil via said normally closed set of relay contacts;
   said first and second electrodes fabricated from magnetic material with one of said contacts permanently magnetized;
   said first and second electrodes positioned adjacent to each other but electrically separated by a spacer creating a space therebetween which may be electrically closed by the presence of an electrolyte; and
   an alarm means responsively connected to said set of normally open contacts.

2. An apparatus as defined in claim 1 wherein said latching relay comprises mechanical means to latch open said normally closed contacts and latch closed said normally open contacts when energized, said contacts adapted to remain in the latched positions after said relay coil is deenergized until mechanically reset.

3. An apparatus as defined in claim 2 wherein said spacer comprises an insulator having a surface area less than said first electrode and said spacer is secured to said first electrode.

4. A moisture sensing apparatus as defined in claim 1 wherein said alarm means comprises a visual warning device and means to intermittently activate said warning device in response to current flow from said set of normally open electrical contacts.

5. A moisture sensing apparatus as defined in claim 4 wherein said visual warning device is a nurse call lamp.

6. An apparatus as defined in claim 1 further comprising:

current limiting means connected between said power source and said relay and electrodes for preventing current flow from exceeding a value which will cause discomfort or electrical shock to a person coming in contact with said electrodes.

7. A moisture sensing apparatus as defined in claim 6, further comprising:
a switch means electrically connected between said current limiting means and said power source whereby said current to said relay may be interrupted.

8. A moisture sensing apparatus as defined in claim 1 wherein a magnetic field exists between said first and second electrodes of sufficient force to hold said electrodes together, further comprising insulating spacer means positioned between said first and second electrodes for creating a space therebetween which may be electrically closed by the presence of an electrolyte.

9. An apparatus as defined in claim 1 wherein said spacer comprises an insulator having a surface area less than said first electrode and said spacer is secured to said first electrode.

10. A moisture sensing apparatus as defined in claim 9 wherein said insulator secured to said first electrode is configured in the form of a ring, further comprising:
a second electrode insulator secured in the center of said second electrode and dimensioned to fit within the center of said first electrode ring insulator.

11. A moisture sensing apparatus as defined in claim 8, wherein said insulating spacer means comprises:
a first insulator relatively narrow with respect to said first electrode, said first insulator secured to said first electrode and positioned off center; and
a second insulator relatively narrow with respect to said second electrode, said second insulator secured to said second electrode and positioned off center whereby the magnetic force between said first and second electrodes will hold said electrodes adjacent to each other with their contact faces parallel but separated by said first and second insulators.

* * * * *